United States Patent
Kulkarni et al.

(10) Patent No.: US 6,548,746 B1
(45) Date of Patent: Apr. 15, 2003

(54) 'DHAWAL', A HIGH ALKALOID PRODUCING PERIWINKLE PLANT

(75) Inventors: Raghavendra Narayan Rao Kulkarni, Lucknow (IN); Kuppusamy Baskaran, Lucknow (IN); Ravoor Shankara Rao Chandrashekara, Lucknow (IN); Suman Preet Singh Khanuja, Lucknow (IN); Mahendra Panduranga Darokar, Lucknow (IN); Ajit Kumar Shasany, Lucknow (IN); Girish Chandra Uniyal, Lucknow (IN); Madan Mohan Gupta, Lucknow (IN); Sushil Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/531,773

(22) Filed: Mar. 21, 2000

(51) Int. Cl.$^7$ .................................................. A01H 5/00
(52) U.S. Cl. ........................ 800/323; 800/298; 800/295
(58) Field of Search .................................. 800/323, 226, 800/295, 298

Primary Examiner—Bruce R. Campell
Assistant Examiner—June Hwu
(74) Attorney, Agent, or Firm—Birch, Stewart, Kolasch & Birch, LLP

(57) ABSTRACT

The invention relates to the development of a new and distinct mutant 'Dhawal' of periwinkle, *Catharanthus roseus*, produced by chemical mutagen treatment of the seeds followed by rigorous selection in a widely cultivated variety 'Nirmal' of *Catharanthus roseus*, said plant being stable, homozygous and produces conspicuously higher herbage and alkaloid yield.

1 Claim, 2 Drawing Sheets

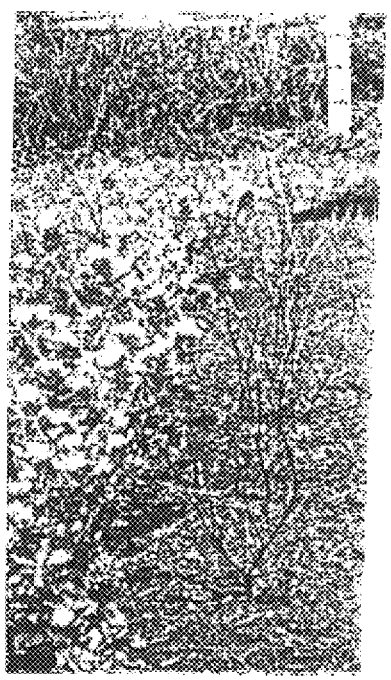
Figure 1 Die back tolerance in 'Dhawal'
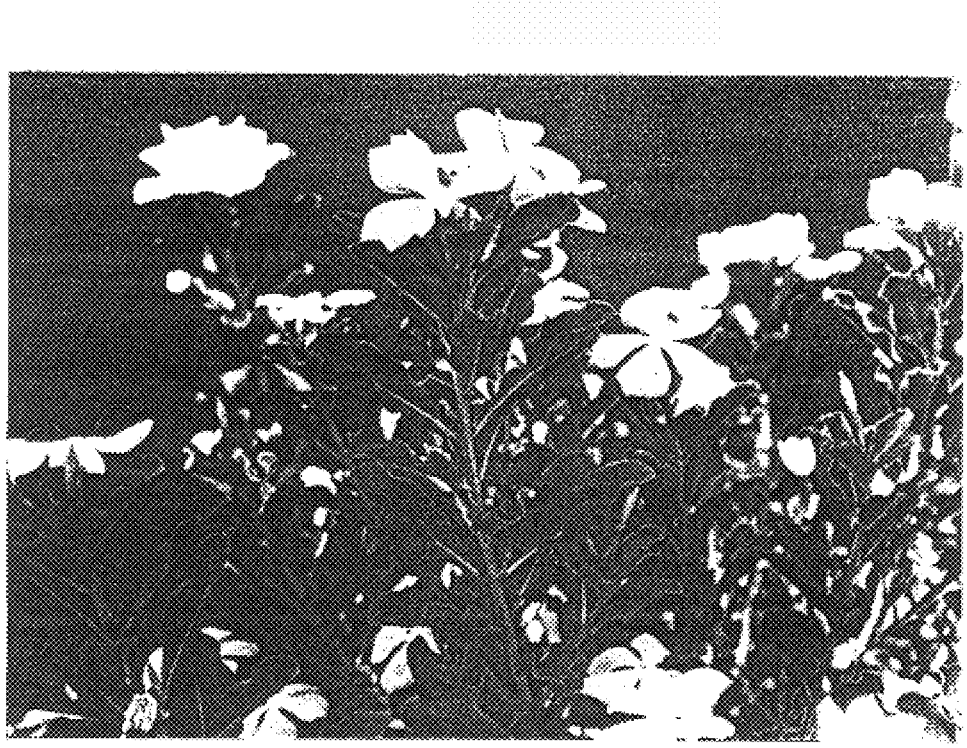
Figure 2 Twigs of 'Dhawal' showing leaves with wavy margins Comparative RAPD Profile of cv Nirmal Vs the plant of invention Dhawal.

M : Molecular weight marker (λ EcoRI + Hind III digest), N : Nirmal, D : Dhawal

```
                          SEQUENCE LISTING

<160> NUMBER OF SEQ ID NOS: 7

<210> SEQ ID NO 1
<211> LENGTH: 10
<212> TYPE: DNA
<213> ORGANISM: Artificial Sequence
<220> FEATURE:
<223> OTHER INFORMATION: Synthetic DNA primer

<400> SEQUENCE: 1
aaatcggagc                                                           10

<210> SEQ ID NO 2
<211> LENGTH: 10
<212> TYPE: DNA
<213> ORGANISM: Artificial Sequence
<220> FEATURE:
<223> OTHER INFORMATION: Synthetic DNA primer

<400> SEQUENCE: 2
gtcctactcg                                                           10

<210> SEQ ID NO 3
<211> LENGTH: 10
<212> TYPE: DNA
<213> ORGANISM: Artificial Sequence
<220> FEATURE:
<223> OTHER INFORMATION: Synthetic DNA primer

<400> SEQUENCE: 3
tgcgcgatcg                                                           10

<210> SEQ ID NO 4
<211> LENGTH: 10
<212> TYPE: DNA
<213> ORGANISM: Artificial Sequence
```

```
<220> FEATURE:
<223> OTHER INFORMATION: Synthetic DNA primer

<400> SEQUENCE: 4
aacgtacgcg                                                              10

<210> SEQ ID NO 5
<211> LENGTH: 10
<212> TYPE: DNA
<213> ORGANISM: Artificial Sequence
<220> FEATURE:
<223> OTHER INFORMATION: Synthetic DNA primer

<400> SEQUENCE: 5
cgggatccgc                                                              10

<210> SEQ ID NO 6
<211> LENGTH: 10
<212> TYPE: DNA
<213> ORGANISM: Artificial Sequence
<220> FEATURE:
<223> OTHER INFORMATION: Synthetic DNA primer

<400> SEQUENCE: 6
ccctgcaggc                                                              10

<210> SEQ ID NO 7
<211> LENGTH: 10
<212> TYPE: DNA
<213> ORGANISM: Artificial Sequence
<220> FEATURE:
<223> OTHER INFORMATION: Synthetic DNA primer

<400> SEQUENCE: 7
ccaagcttgc                                                              10
```

'DHAWAL', A HIGH ALKALOID PRODUCING PERIWINKLE PLANT

FIELD OF INVENTION

The present invention relates to the development of a new and distinct mutant of periwinkle, *Catharanthus roseus*, called 'Dhawal' produced by chemical mutagen treatment of the seeds and selection in widely cultivated variety 'Nirmal' of *Catharanthus roseus*. The mutant thus selected was selfed for several generations to achieve the homozygous true to the type plants maintaining stability of the genotype from generation to generation. The finally selected mutant, homozygous, selfed plant can be propagated by seeds obtained from self-pollination and also by terminal stem cuttings. Seeds of the variety 'Dhawal' have been deposited Sep. 12, 2002 under the Accession Number NCIMB 41147 at the international depository authority NCIMB (National Collections of Industrial, Food and Marine Bacteria) located at 23 St. Machar Drive, Aberdeen, AB24 3RY, SCOTLAND. The plant of the present invention is stable for commercial cultivation, which maintains the stability of the improved characters.

BACKGROUND OF THE INVENTION

The genus Catharanthus belongs to the botanical family Apocynaceae, subfamily, Plumeriodae, tribe Plumariae and subtribe Alstoniiae. The first known species, *C roseus* was included in the genus Vinca (*V. rosea*) by Linnaeus. It was also called as *Lochnera roseus*. Originally endemic to Madagascar, this species has become naturalised in tropical countries and is generally grown as an ornamental plant.

This plant has been found to be a good source of anti-cancer alkaloids, vincristine (VCR) and vinblastine (VLB) and an anti-hypertension alkaloid, ajmalicine. The estimated value of the annual world demand for these alkaloids, VLB, VCR and ajmalicine is about $12 m, 3.5 m and 10 m respectively. Three varieties of the species namely, var. *roseus* with pink or rose coloured flowers, var. *albus*, with white flowers and var. *ocellatus* with white flowers and purple centre are known in *C. roseus*. A superior cultivar named, 'Nirmal' with high level of field resistance to die-back disease has been developed and released earlier by CIMAP.

Seeds obtained through self-pollination can propagate the genotypes of periwinkle. Terminal stem cuttings can also be useful for the propagation purpose.

The range of characteristics that are found among plants of this species suggest that further improvement by known breeding methods to obtain plants of unusual and valuable character is possible. The plant 'Dhawal' of this invention involves such an improvement. The present invention relates to a new and distinct plant called 'Dhawal' periwinkle, *Catharanthus roseus* as an induced mutant of variety 'Nirmal'. These plant combines the characters of improved alkaloid yield with tolerance to the die back disease. This plant offers growers improved and high alkaloid yielding variety having high degree of resistance to dieback disease.

OBJECTS

The main object of the invention is to develop a new variety of periwinkle called 'Dhawal' through mutagenesis, such that the plant is stable and suitable for commercial cultivation and produces higher herbage yields alkaloids in higher quality than the known and existing varieties.

SUMMARY OF THE INVENTION

The present invention relates to the development of a new and distinct mutant 'Dhawal' of periwinkle, *Catharanthus roseus*, produced by mutagenesis and selection from the seeds of widely cultivated variety of *Catharanthus roseus*, Nirmal. The mutant thus isolated and selected was selfed for several generations to achieve homozygous true to type plants maintaining stability of the genotype from generation to generation. The plant of invention is stable for commercial cultivation, maintains the stability of the improved characters. The plant produces higher herbage and alkaloid compared to other existing varieties.

DETAILED DESCRIPTION

Accordingly, the invention provides a new and distinct high alkaloid and greater herbage yielding plant 'Dhawal'. It is distinct from the known variety of *Catharanthus roseus*, and is developed through chemical mutagen treatment.

The novel plant 'Dhawal' has the following combination of characteristics:

(a) light green to grayish green (emerald green 758/1) pubescent leaves with distinctly undulating leaf margin,
(b) green stem, white flowers,
(c) leaf yield of 1352 to 2557 kg/ha,
(d) yielding 0.89 to 1.40%, alkaloids in leaves,
(e) yielding 1.60 to 2.22%, alkaloids in roots,
(f) resistant to die-back disease,
(g) randomly amplified polymorphic DNA (RAPD) profile for polymerised chain reaction (PCR) amplified DNA segment using 4 primers (OPT 06, 09, 16 and 17) distinct from the other existing varietie(s), and
(h) higher herbage, alkaloid yield as compared to other existing varietie(s).

Accordingly, the present invention provides a hitherto unknown and distinct high alkaloid producing *Catharanthus roseus* plant called 'Dhawal' having the following combination of characters:

(a) plant height of 65–75 cm,
(b) light green to grayish green (emerald green 758/1) pubescent leaves with distinctly undulating leaf margin,
(c) green stem,
(d) white flowers,
(e) field resistance to die back disease.
(f) high leaf yield of 1352 to 2557 kg/ha,
(g) 0.89 to 1.40% of total alkaloids in leaves,
(h) 1.60 to 2.22% of total alkaloids in roots
(i) randomly amplified polymorphic DNA (RAPD) profile for polymerised chain reaction (PCR) amplified DNA segment using 4 primers (OPT 06, 09, 16 and 17) distinct from the other existing varietie(s), and
(j) higher herbage, alkaloid yield as compared to any other existing varietie(s).

The plant of invention 'Dhawal' is thus distinct, different, novel and has tremendous commercial application due to improved alkaloid content.

BRIEF DESCRIPTION OF THE DRAWINGS

The invention is described in detail with reference to the accompanying drawings wherein:

FIG. 1 is a photograph that depicts the die-back tolerance in periwinkle plants of the invention 'Dhawal'.

FIG. 2 is a photograph of the twigs of the plant 'Dhawal' of the invention. This figure clearly shows that the leaves have wavy margins.

Figure 3:
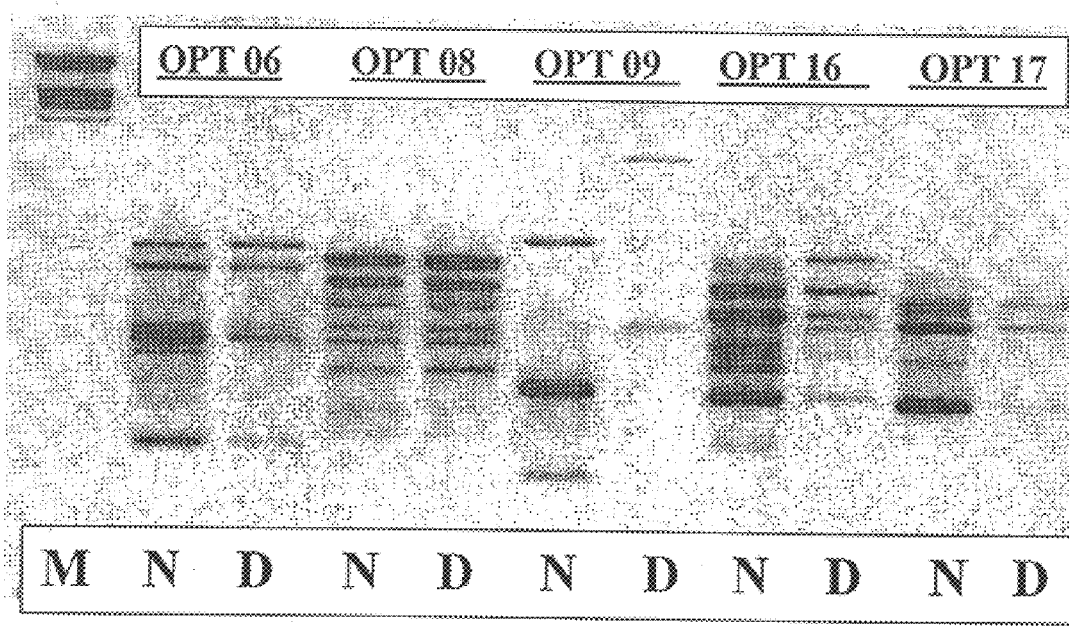
FIG. 3 depicts the RAPD profile of 'Dhawal'.

Further, the invention is described in detail hereinbelow with reference to the following examples which are provided merely to illustrate the invention and these should not be construed or limit the scope thereof in any manner.

The new plant of this invention is a periwinkle mutant named 'Dhawal', which was developed in a planned breeding programme conducted by the applicants at Central Institute of Medicinal and Aromatic Plants, Lucknow, India and its field station at Bangalore with the main objective to obtain a mutant line with high content of leaf alkaloids. For this purpose, overnight pre-soaked seeds of a 'die back' resistant variety 'Nirmal', were treated with 0.04% to 0.06% (v/v) unbuffered aqueous solutions of the chemical mutagen, N-nitroso-N-ethyl urea (NEU) and 0.6 to 0.8% (v/v) unbuffered aqueous solutions of the chemical mutagen, ethyl methanesulphonate (EMS) independently for six hours. The plant of this invention was selected in the second-generation ($M_2$) of plants obtained from the 0.06% NEU treatment. The plant of this invention was conspicuously different from other plants due to its different leaves, which had wavy leaf margins. It was selected for further observation and testing for other characteristics. This plant was tested along with the parental variety Nirmal in replicated trials in three generations, $M_3$, $M_4$ and $M_5$ following its identification. In all the three trials, it was found to have higher content and yield of leaf alkaloids than the parental variety. It was found to possess similar level of resistance to 'die back' like the parental variety 'Nirmal' as shown in FIG. 1. To fix the improved characters the applicants selfed the plants for three generations and selected homozygous plants maintaining the characters.

Evidence of Uniformity and Stability

The plant of invention 'Dhawal' has demonstrated stability and uniformity for its distinctly different leaf morphological character and higher alkaloid yield than the parental variety, 'Nirmal' during its evaluation across three generations following its selection in 1992.

Type and Frequency of Variants During Reproduction and Multiplication

No variant was found during its multiplication and testing throughout the three generations after its selection in 1992 and the plant is maintaining the improved characters when propagated through the selfed seeds.

Statement of Distinction

The plant of invention 'Dhawal' possesses thin leaves with undulating or wavy leaf margin to distinguish it from the improved variety 'Nirmal' morphologically. This is shown in FIG. 2.

RAPD analysis: The plant of invention was characterized and compared at DNA level through RAPD analysis. The RAPD profiles of Nirmal and Dhawal were compared with 27 random primers. Twenty random primers were procured from Operon Technologies, USA (OPT 01 to 20) and the rest 6 primers with the sequences AAATCGGAGC (SEQ ID NO: 1), GTCCTACTCG (SEQ ID NO: 2), TGCGCGATCG (SEQ ID NO: 3), AACGTACGCG (SEQ ID NO: 4), CGGGATCCGC (SEQ ID NO: 5), CCCTGCAGGC (SEQ ID NO: 6), CCAAGCTTGC (SEQ ID NO: 7), were synthesized in the laboratory. From these primers OPT 10 did not respond. The molecular profiles of the plant of invention could be differentiated only with 4 primers (OPT 06, 09, 16 and 17) and similarity index between Dhawal and Nirmal was calculated to be 0.945. Thus the primers OPT 06, 09, 16 and 17 can be conveniently used for differentiating the plant of invention from the other varieties.

Objective Description of the Plant 'Dhawal'(NEU 1–7)

| | |
|---|---|
| 1. Genus | Catharanthus |
| 2. Species | *roseus* (L.) G. Don. |
| 3. Family | Apocynaceae |
| 4. Common name | Periwinkle |
| 5. Plant name | 'Dhawal' |
| 6. Plant height | 65–75 cm |
| 7. Growth habit | Erect |
| 8. No of primary branches | 7–10 |
| 9. Stem colour | Green |
| 10. Leaf | |
|     Colour | Emerald green 758/1 (Horticultural colour Chart II, 1941 issued by the British Colour Council in collaboration with Royal Horticultural Society) |
|     Shape | Oblong oval |
|     Texture | Pubescent, thin |
|     Margin | Undulating or wavy |
|     Leaf length | 3.9 cm (4.2–5.0 cm) |
|     Leaf breadth | 2.1 cm (2–2.5 cm) |
| 11. Flower | Auxillary, two in number |
|     Colour | White |
|     Petal length | 1.7 cm |
|     Petal breadth | 1.3 cm |
|     Length of corolla tube | 2.5 cm |
|     Length of style | 1.0 cm |
|     Pollen fertility | 90% |
| 12. Fruit | |
|     Colour | Emerald green 785/1 |
|     Texture | Pubescent |
|     Follicle length | 2.9 cm |
|     Seed per follicle | 21 |
| 13. Seeds | |
|     100 seed weight | 120 mg |
| 14. Disease resistance | Moderately resistant to dieback |
| 15. Total alkaloid content | |
|     Leaf | 0.89–1.4% |
|     Root | 1.60–2.22% |

The mutant strain Dhawal was developed at Central Institute of Medicinal and Aromatic Plants (CIMAP), Lucknow, India and its field station at Bangalore which could be distinguished from the existing varieties morphologically and through the DNA profile fingerprint which is unique and distinct. Further the performance of the plant of invention was checked and compared in the $M_3$ (Table 1), $M_4$ (Table 2), $M_5$ (Table 3) generation and was found to be yielding higher amount leaf and alkaloids consistently. In addition, the plant was checked for leaf and alkaloid yields in different locations, Lucknow, India (Table 4) and Bangalore and found to be superior to the existing improved variety 'Nirmal'.

TABLE 1

Performance of the plant 'Dhawal' in $M_3$ generation (1992–93)

| Trait | 'Dhawal' | 'Nirmal' |
|---|---|---|
| 1. Leaf yield (g/plant) | 39.8 | 35.7 |
| 2. Root yield (g/plant) | 7.2 | 9.2 |
| 3. Total alkaloids in leaves (%) | 1.30 | 0.85 |
| 4. Total alkaloid in roots (%) | 1.65 | 1.65 |
| 5. Total leaf alkaloid yield (g/plant) | 0.51 | 0.30 |
| 6. Total root alkaloid yield (g/plant) | 0.11 | 0.15 |

TABLE 2

Performance of the plant 'Dhawal' in $M_4$ generation (1993–94)

| Trait | 'Dhawal' | 'Nirmal' |
|---|---|---|
| 1. Leaf yield (kg/ha) | 2557 | 2590 |
| 2. Root yield (kg/ha) | 622 | 617 |
| 3. Total alkaloids in leaves (%) | 1.12 | 0.83 |
| 4. Total alkaloid in roots (%) | 1.60 | 1.58 |
| 5. Total leaf alkaloid yield (kg/ha) | 28.6 | 21.4 |
| 6. Total root alkaloid yield (kg/ha) | 9.9 | 9.7 |

TABLE 3

Performance of the plant 'Dhawal' in $M_5$ generation (1994–95)

| Trait | 'Dhawal' | 'Nirmal' |
|---|---|---|
| 1. Leaf yield (kg/ha) | 1352 | 1152 |
| 2. Root yield (kg/ha) | 449 | 472 |
| 3. Total alkaloids in leaves (%) | 1.40 | 1.13 |
| 4. Total alkaloid in roots (%) | 1.74 | 1.77 |
| 5. Total leaf alkaloid yield (kg/ha) | 18.9 | 13.0 |
| 6. Total root alkaloid yield (kg/ha) | 7.8 | 8.3 |

TABLE 4

Performance of the plant of invention 'Dhawal' at Lucknow

| Trait | 'Dhawal' | 'Nirmal' (Parent) |
|---|---|---|
| 1. Leaf yield (kg/ha) | 2155 | 2310 |
| 2. Root yield (kg/ha) | 545 | 386 |
| 3. Total alkaloids in leaves (%) | 0.89 | 0.70 |
| 4. Total alkaloid in roots (%) | 2.22 | 2.12 |
| 5. Total leaf alkaloid yield (kg/ha) | 19.2 | 16.2 |
| 6. Total root alkaloid yield (kg/ha) | 12.1 | 8.2 |

What is claimed is:

1. A new and distinct high alkaloid producing *Catharanthus roseus* plant called 'Dhawal' having NCIMB accession number 41147, and having the following combination of characteristics:

(a) plant height of 65–75 cm,
    (b) light green to grayish green (emerald green 758/1 color designation from the "Horticultural Colour Chart II") pubescent leaves with distinctly undulating leaf margin,
    (c) green stem,
    (d) white flowers,
    (e) field resistance to die back disease,
    (f) high leaf yield of 1352 to 2557 kg/ha,
    (g) 0.89 to 1.40% of total alkaloids in leaves,
    (h) 1.60 to 2.22% of total alkaloids in roots,
    (i) a randomly amplified polymorphic DNA (RAPD) profile distinct from the variety 'Nirmal' when the DNA is polymerase chain reaction (PCR) amplified by four primers selected from the group consisting of: OPT 06, 09, 16 and 17, and
    (j) higher herbage and alkaloid yield as compared to the variety 'Nirmal'.

* * * * *